(12) United States Patent
King

(10) Patent No.: US 6,615,661 B2
(45) Date of Patent: Sep. 9, 2003

(54) ULTRASOUND SORTING OF WEANLING CALVES AND IDENTIFICATION OF TENDERNESS INDICATORS

(76) Inventor: Rethel C. King, 4594 Union Rd., Harrison, AR (US) 72601

( * ) Notice: Subject to any disclaimer, the term of this patent is extended or adjusted under 35 U.S.C. 154(b) by 0 days.

(21) Appl. No.: 09/870,150

(22) Filed: May 30, 2001

(65) Prior Publication Data

US 2002/0178820 A1 Dec. 5, 2002

(51) Int. Cl.$^7$ .......................... G01N 29/00; A61B 8/00
(52) U.S. Cl. .......................... 73/602; 73/600; 600/437; 600/439; 600/449
(58) Field of Search .......................... 73/602, 597, 598, 73/599, 600; 600/437, 439, 449, 442, 443, 445, 453, 459; 382/110, 194

(56) References Cited

U.S. PATENT DOCUMENTS

| | | | |
|---|---|---|---|
| 3,496,764 A | 2/1970 | Stouffer | 73/67.8 |
| 3,579,716 A | 5/1971 | Stouffer et al. | 17/45 |
| 3,603,303 A | 9/1971 | Stouffer | 128/2 |
| 4,099,420 A | 7/1978 | Stouffer et al. | 73/629 |
| 4,359,055 A | 11/1982 | Carlson | 128/660 |
| 4,359,056 A | 11/1982 | Carlson | 128/660 |
| 4,785,817 A | 11/1988 | Stouffer et al. | 128/660 |
| 5,079,951 A | 1/1992 | Raymond et al. | 73/602 |
| 5,140,988 A | 8/1992 | Stouffer et al. | 128/660.01 |
| 5,208,747 A | 5/1993 | Wilson et al. | 364/413.25 |
| 5,303,708 A | 4/1994 | Stouffer | 128/660.01 |
| 5,316,003 A | 5/1994 | Stouffer | 128/662.03 |
| 5,339,815 A | 8/1994 | Liu et al. | 128/660.01 |
| 5,353,796 A | 10/1994 | Schroeder et al. | 128/660.01 |
| 5,520,183 A | 5/1996 | Lake et al. | 128/660.01 |
| 5,573,002 A | 11/1996 | Pratt | 128/660.07 |
| 5,625,147 A | 4/1997 | Miles et al. | 73/597 |
| 5,685,307 A | 11/1997 | Holland et al. | 128/660.01 |
| 5,836,880 A | 11/1998 | Pratt | 600/443 |
| 5,872,314 A | 2/1999 | Clinton | 73/602 |
| 5,941,825 A | 8/1999 | Lang et al. | 600/449 |
| 5,944,598 A * | 8/1999 | Tong et al. | 452/158 |
| 5,960,105 A | 9/1999 | Brethour | 382/141 |
| 6,012,332 A | 1/2000 | Schafer | 73/579 |
| 6,084,407 A * | 7/2000 | Ellis | 324/300 |
| 6,099,473 A * | 8/2000 | Liu et al. | 600/449 |
| 6,123,451 A * | 9/2000 | Schaefer et al. | 374/45 |
| 6,167,759 B1 | 1/2001 | Bond et al. | 73/602 |
| 6,170,335 B1 | 1/2001 | Clinton | 73/629 |

* cited by examiner

*Primary Examiner*—Helen Kwok
*Assistant Examiner*—Jacques Saint-Surin
(74) *Attorney, Agent, or Firm*—Joseph T. Guy; Nexsen Pruet Jacobs & Pollard, LLC

(57) ABSTRACT

A method and system for determining meat quality in cattle is provided. In preferred embodiments the method comprises obtaining an ultrasound measurement of a cattle specimen between the 12$^{th}$ rib and 13$^{th}$ rib at weaning age. The ultrasound measurement is utilized to extrapolate a harvest quality parameter. Based on the harvest quality parameter, and preferably a yield grade, the specimen is categorized. Particularly preferred harvest quality parameters are ribeye area, fat thickness, intramuscular fat and ribeye shape. Methods for determining tenderness, stress and intramuscular fat are described and claimed.

2 Claims, 3 Drawing Sheets

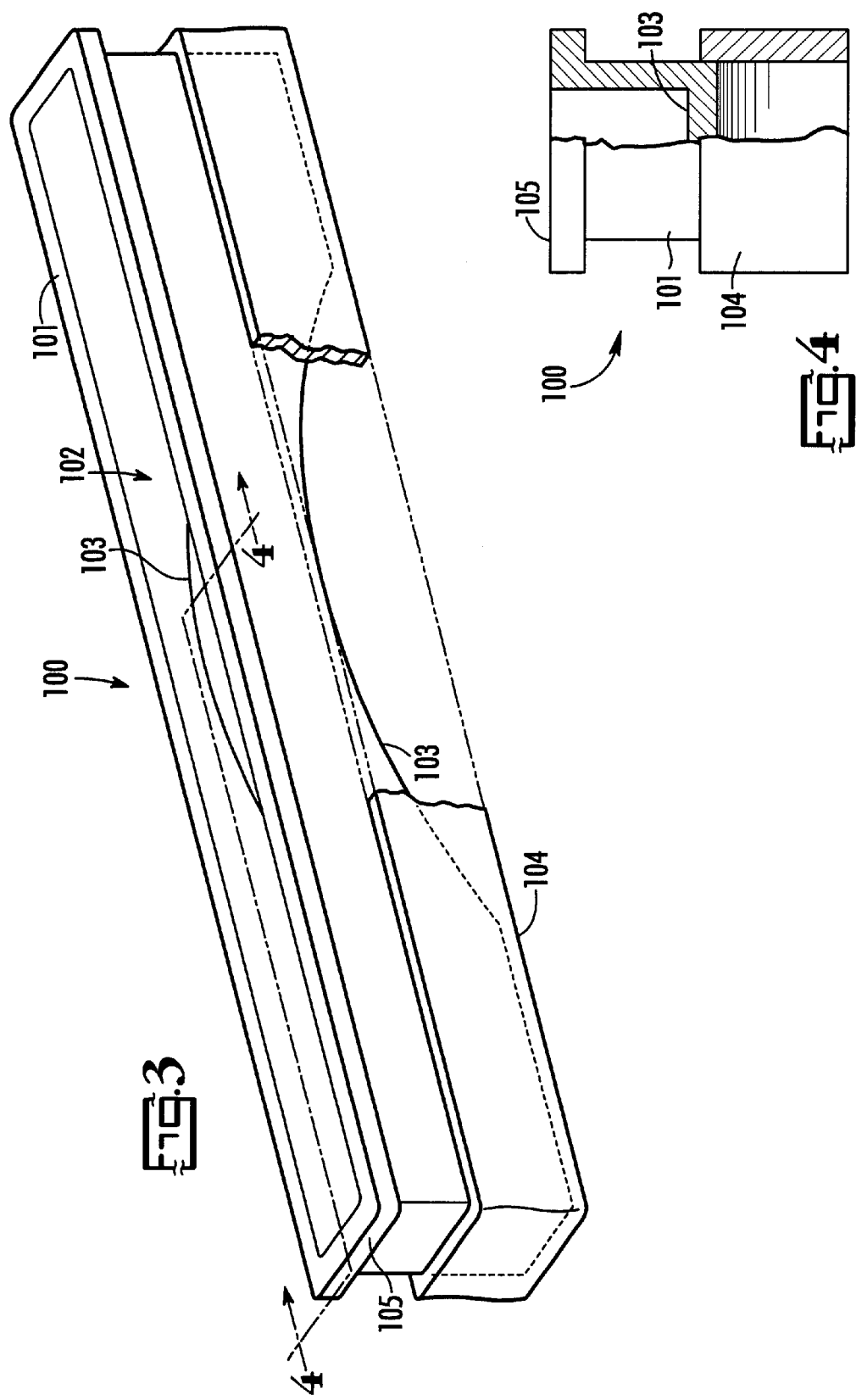

ULTRASOUND SORTING OF WEANLING CALVES AND IDENTIFICATION OF TENDERNESS INDICATORS

TECHNICAL FIELD

The present invention is related to the use of ultrasound to sort calves at weaning based on predicted meat quality at harvest. More specifically, this invention is related to an ultrasound method, and apparatus, which improves the sorting of calves and the ability to predict carcass meat quality, particularly the tenderness of the meat.

BACKGROUND

It has long been the desire of cattle producers to predict the eventual meat quality of beef cattle at an early age. Particularly, it has been the desire to determine meat quality early enough to allow the cattle producer to optimize the herd for maximum financial return.

Carcass measurement has long been practiced in the art. Carcass testing can provide valuable information utilizing pattern recognition procedures to insure that the available meat is optimized. While carcass measurements are advantageous, it eliminates the possibility of utilizing exemplary specimens in breeding programs or of extending harvest time for maximum financial gain. Some specimens may return a higher financial return if allowed to develop slightly longer or the financial return may be higher if slaughter is expedited. Any form of carcass testing eliminates further optimization of the financial return or of meat quality. Exemplary references disclosing the use of carcass measurements include: U.S. Pat. Nos. 3,603,303; 4,099,420; 4,758,817; 5,303,708; 6,099,473 and 5,079,951.

Presently, in the beef industry, ultrasound technology is not used to evaluate seed stock cattle for carcass merit until approximately one year of age. The prior thought has been that cattle needed to achieve at least this level of physiological maturity to adequately evaluate meat quality. However, if seed stock cattle could be reasonably evaluated at the time of weaning, substantial economic impact could result. There are no current methods in place to determine potential tenderness in standing cattle. The National Cattlemen's Beef Association (NCBA) has identified tenderness problems of beef as one of the major contributors to customer dissatisfaction. The ability to determine potential tenderness of a carcass via live animal ultrasound could tremendously enhance genetic selection and ultimately the uniformity of the beef.

It is now standard practice to fatten the entire herd of cattle prior to harvest. This is costly and could result in fattening of inferior specimens which could return a loss or insufficient profit to justify the expense. The current methods of testing typically measure the size of the longissimus dorsi muscle as well as the internal and external fat content just prior to harvest. These methods are not applicable prior to the full regiment of feed has been completed since these parameters are a direct result of the feed program. Even if the size is optimum and the fat content is optimum the meat may still be tough. It would be a major advantage if the meat quality could be evaluated prior to the expense of feeding cattle for harvest.

Size measurement techniques, wherein the size or shape of the longissimus dorsi muscle, or ribeye, is determined are legion in number. The size of the longissimus dorsi muscle relative to the fat thickness, or total weight, are correlated to meat yield but not necessarily meat quality parameters such as tenderness. Measurements of muscle size, or shape, utilizing ultrasound techniques are disclosed in U.S. Pat. Nos. 3,496,764; 4,359,055; 4,359,066, 6,012,332; 5,520,183; 5,353,796; 5,339,815; 5,960,105 and 5,914,825. These techniques are only useful just prior to harvest since the amount of fat is clearly a function of the feeding regiment and meat quality includes additional parameters.

Indirect methods of determining meat quality based on the fat content, or by correlation to a panel of human analyst, have been described yet these are still not predictive of future meat quality parameters such as tenderness. Exemplary disclosures are provide in U.S. Pat. Nos. 5,685,307; 5,208,747 and 5,625,147.

The physical transducer, methods of insuring proper placement, and signal processing procedures for standing cattle just prior to harvest are disclosed in U.S. Pat. Nos. 5,836,880; 5,872,314; 6,170,335; 5,316,003; 5,573,002 and 6,167,759. None of the cited references can provide a predictive measurement of meat quality early in the life cycle of the specimen. Specifically, there is not available in the art a system which provides the ability to measure cattle at weaning to predict the future quality parameters such as tenderness.

Even with the advanced nature of the art there is still a desire to predict, preferably at weaning, the eventual tenderness of the meat. Heretofore, this has eluded those of exemplary skill in the art.

There has been a long felt desire in the art for a non-invasive measurement technique, and apparatus therefore, which will allow for the predictive determination of meat tenderness and other properties related to meat quality thereby allowing for optimized financial return and improved quality of the beef early in the life cycle of the cattle.

SUMMARY

It is an object of the present invention to provide a method and system for predicting meat quality of cattle early in the life cycle thereby increasing the return at harvest.

It is another object of the present invention to provide a method for determining the quality of meat, specifically tenderness, prior to harvest. More preferably, the tenderness can be determined at weaning thereby allowing herd discrimination to be practiced.

It is yet another object of the present invention to provide a method and system which can allow for accurate prediction of meat quality with standing cattle thereby allowing exemplary specimen to be recognized prior to harvest. A particular advantage is the ability to utilize exemplary specimen in breeding programs which can increase the overall value of the herd and return on the investment.

These and other advantages, as will be realized from the teachings herein are provide in a method for categorizing cattle by meat quality. The method comprises obtaining an ultrasound measurement of a cattle specimen between the $12^{th}$ rib and $13^{th}$ rib at weaning age. The ultrasound measurement is utilized to extrapolate a harvest quality parameter. Based on the harvest quality parameter, and preferably a yield grade, the specimen is categorized. Particularly preferred harvest quality parameters are ribeye area, fat thickness, intramuscular fat and ribeye shape.

Another embodiment of the present invention is provided in a method for categorizing cattle by meat quality. The method comprises obtaining an ultrasound measurement of a cattle specimen at a location of approximately ¾ of the length of a longissimus dorsi muscle between the 12$^{th}$ rib and 1$^{st}$ lumbar. Tenderness is determined based on the ultrasound measurement and the specimen is categorized by the tenderness. In a particularly preferred embodiment the tenderness is determined by the angle of connective tissue deposition in a longissimus dorsi muscle. In another preferred embodiment the tenderness is proportional to the connective tissue thickness.

Yet another embodiment is provided in a process for predicting meat tenderness in an animal. The process comprises the steps of a) obtaining a longitudinal ultrasound measurement of a longissimus dorsi muscle; b) determining the angle of the connective tissue in the longissimus dorsi muscle relative to the centerline of the animal; and c) assigning a tenderness based on the angle of the connective tissue.

Yet another embodiment is provided in a system for predicting meat tenderness wherein the system comprises an ultrasound system for obtaining an image of a longissimus dorsi muscle and a measurement device for determining an angle of connective tissue in the longissimus dorsi muscle from the image.

BRIEF DESCRIPTION OF THE DRAWINGS

FIG. 3 is a partial cut-away perspective view of a conforming guide which has exemplary utility in the present invention.

FIG. 4 is a partial cut-away side view of the conforming guide illustrated in FIG. 3.

DETAILED DESCRIPTION

The invention will be described with reference to the drawings wherein similar elements are numbered accordingly.

Figure 1:
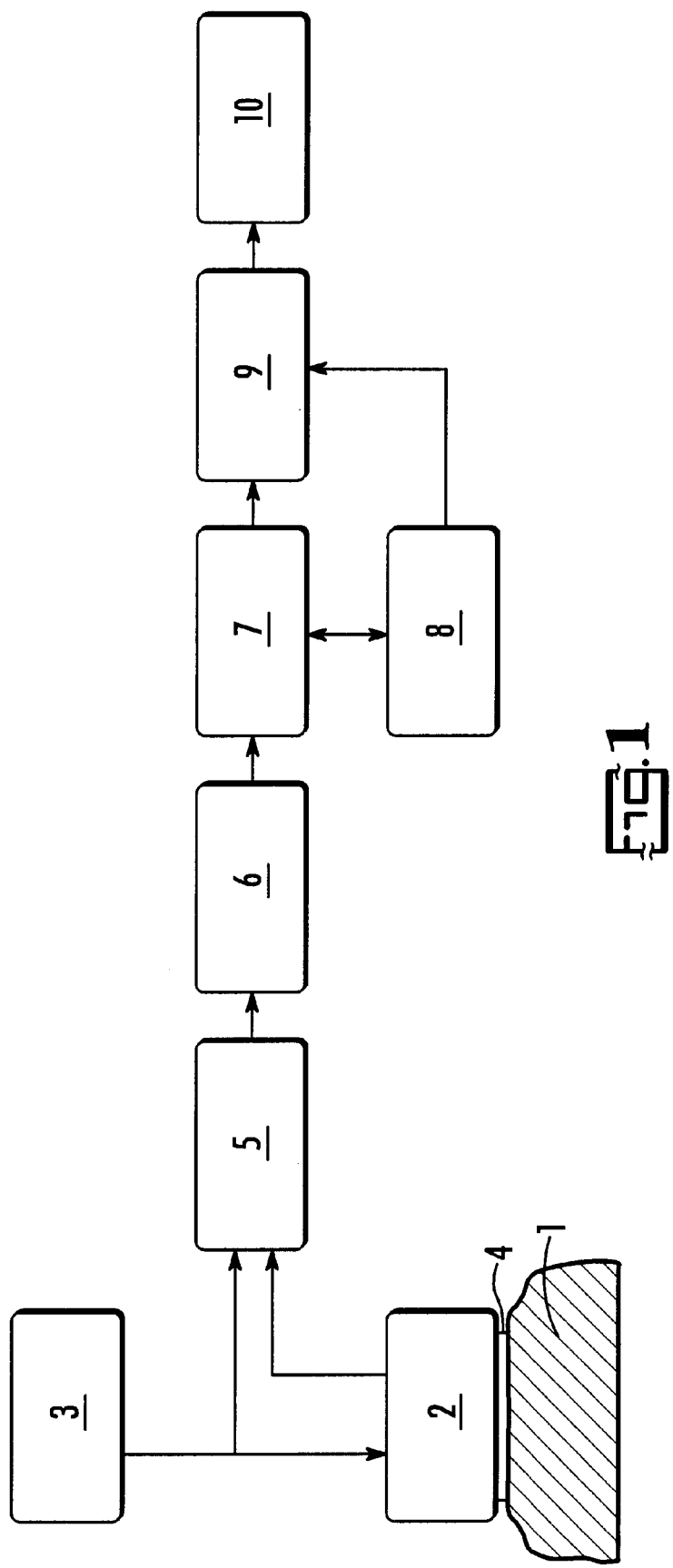
FIG. 1 is a schematic illustration of the system of the present invention.

An ultrasound system for measuring meat quality is illustrated schematically in FIG. 1. In FIG. 1, the specimen, 1, is in functional contact with an ultrasound transducer, 2. A pulse generator, 3, transmits a series of high voltage pulses which the ultrasound transducer, 2, converts to ultrasound pulses in the preferred frequency range of 3.0–7.5 MHz. Most preferably the transducer transmits at a frequency of approximately 3.5 MHz. The ultrasound pulses are transmitted into the specimen, 1. Pulse generators are commercially available and not limited herein. While not limited thereto, a particularly suitable pulse generator is an ALOKA Model SSD 500V available from ALOKA USA. Transducers are commercially available and not limited herein. While not limited thereto, a particularly suitable transducer is a Model UST 5044 3.5 MHz also available from ALOKA USA.

It is most preferable to utilize a conductive fluid, 4, between the transducer, 2, and the specimen, 1, to insure adequate transmittal of ultrasound waves. While not limited herein common conductive fluids include water, vegetable oil and mineral oil. In a preferred embodiment, a conforming guide is employed as described further herein.

The transducer transmits ultrasounds and receives an echo, or backscatter, of the ultrasound waves. The echo time and energy is based on the composition of the material through which the ultrasound transits. The echo signal is related to boundary structures, tissue density and other factors as well known in the art. In the present invention it is most desirable to utilize B-mode ultrasound, also referred to as brightness mode, which provide two dimensional images of the scanned field. A-mode ultrasound, also referred to as amplitude mode, provides a projected view and is less desirable due to the difficulty associated with differentiating layers and particularly the thickness of individual layers. The echoed ultrasound wave is received by the transducer, 2. The transducer generates an output signal which is proportional to the echoed ultrasound wave. An receiver/amplifier, 5, receives the voltage pulse from the pulse generator, 3, and the output signal from the transducer, 2. The output signal from the transducer is amplified and output to an analog to digital converter (A/D converter), 6. The digital signal is captured by a computer, 7. A storage device, 8, preferably integral to the computer, can store raw data directly from the A/D converter. A data processor, 9, determines properties of the sample from the digital data and transmits these properties to a display device, 10.

Receivers, amplifiers and image capture devices, either as a single device or a combination of devices, are readily available from a variety of commercial sources. While not limited thereto, an Imagination Model 2019 image capture board available from Zedec Vision Systems is eminently suitable for demonstration of the invention as set forth herein. Analog to digital converters, computers, and data processors are all well know and widely available from commercial sources. The present invention is not dependent upon the selection of these devices. While described herein as independent elements it is understood that a single system can be utilized which comprises those elements necessary to accomplish the task described without departing from the invention. While not limited thereto, an ultrasound system commercially available from ALOKA USA, adapted to select the parameters of the image described herein can be used to demonstrate the teachings of the present invention. Display devices are commercially available from many sources. Display devices include hard copy devices such as printers, and soft copy devices such as computer screens, monitors and the like. In one embodiment the storage device, 8, is capable of storing digital data directly from the computer, 7. In another embodiment, the storage device can store the properties which have been determined from the digital data by the data processor, 9. Data storage devices are well known in the art and not limited herein. Particularly preferred are storage devices such as hard drives, magnetic or optical media, paper printouts, random access memory storage devices and the like.

Figure 2:
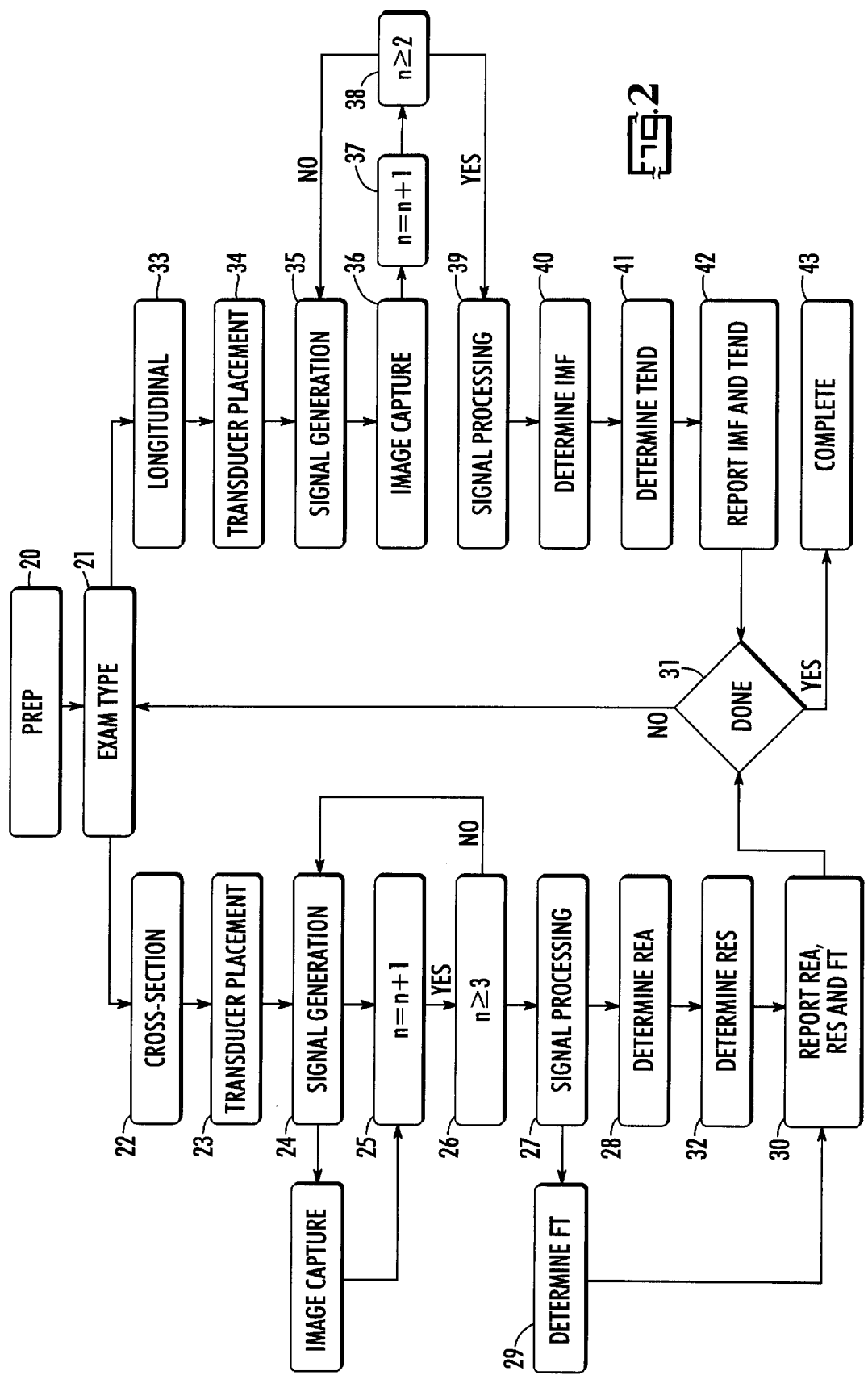
FIG. 2 is a flow chart representing a preferred method of determining quality parameters of cattle.

A flow chart illustrating the procedure for determining meat quality is provided in FIG. 2.

Prior to analysis the specimen is prepared at block 20. Preparation preferably includes manual cleaning of the scanning site and application of conductive fluid. It is most preferable to remove surface hair from the scanning site to insure adequate contact between the transducer and the skin of the specimen. After sample preparation, 20, a choice is made between a cross-sectional exam or a longitudinal exam, at block 21.

If a cross-sectional exam is chosen, initiating with block, 22, the transducer is placed in the proper position perpendicular to longissumus dorsi muscle and the vertebrae and between the 12$^{th}$ and 13$^{th}$ rib at block 23. The position allows for a cross-sectional view of the longissimus dorsi muscle.

A signal is generated, at block 24, which causes the transducer to emit an ultrasound signal, preferably at approximately 3.5 MHz. The ultrasound signal is back scattered from the specimen with back scattered times and intensities based on the anatomical features therein. The back scattered, or echoed, signal is received by the transducer. After acquiring a signal a counter is advanced at block 25. If three landmark samples have been acquired, as indicated at block 26, the signal processing is initiated at block 27. Otherwise, additional readings are recorded.

Cross-sectional image capture allows for determination of fat thickness (FT), ribeye area (REA) and a ribeye shape score (RES).

The ribeye area is determined, at block 28, by the cross sectional imaging measurements taken at the three landmarks in the longissimus muscle image taken between the $12^{th}$ and $13^{th}$ rib location. The three landmarks utilized are the upper fat line between the longissimus dorsi muscle and the back fat, the vertabrae process and the junction of the lateral portion of the longissimus dorsi muscle and the intercostal junction. If the three landmark areas are not present the image is not accepted for interpretation. The processor also calculates the $12^{th}$ through $13^{th}$ rib back fat thickness (FT) from the ultrasound cross-section between the $12^{th}$ and $13^{th}$ rib location. The system determines FT, at block 29, based on identification of the distance between the second interface line from the top of the image to the bottom of the third interface line. This measurement may be used as an indicator of yield grade in weaned calves, yearling cattle, and fed cattle to aid in determining appropriate management level and to validate stress and performance. The system also calculates longissimus muscle circumference which is also referred to as ribeye shape (RES), at block 32, to determine area, muscle depth and muscle length based on a cross-reference REA determination. The REA, FT and RES are reported at block 30. The RES of weanling age calves is a useful parameter for predicting the final yield grade potential and calves may be ranked according to the RES. The FT, REA and RES reports can be stored in a retrievable database, as is common with computers, printed or displayed on a monitor. It is most preferred that the FT, REA and RES reports be displayed on a monitor at chute side to allow for instant decisions. It is also preferred that the FT, REA and RES be stored, or printed, such that a record can be maintained as would be understood to be desirable. It would be apparent that the processor allows additional information input including a specimen identifier, weight, age, and other parameters typical in the raising and maintaining of beef cattle.

If the measurement is complete, at block 31, the process is completed at block 43. Otherwise, additional exam types can be initiated at block 21.

If a longitudinal exam is requested, as indicated at block 33, the transducer is repositioned at block 34 such that a longitudinal image of the longissimus muscle can be captured between the $12^{th}$ rib and $1^{st}$ lumbar vertebrae. A signal is generated at block 35 and image is captured at block 36. It is most preferably that at least two data points be acquired, as indicated by the counter, at block 37, and test block, 38. The system preferably determines landmarks for obtaining a suitable image. Preferably at least two separate images are captured at block 36 from separate locations. The signal is processed at block 39 wherein the IMF is determined through averaging the values from each location for pixel density and texture at block 40. In a preferred embodiment a minimum of two separate IMF images are required before a calculation can be conducted.

A determination of tenderness (TEND) is preferably conducted at the same site as the calculation of IMF at block 41.

A longitudinal ultrasonic image of the longissimus dorsi is utilized to determine tenderness. A tenderness score based on the angle of connective tissue deposition in the longissimus dorsi muscle and from the connective tissue density. It has been determined that the angle of connective tissue deposition is correlated to the angle of connective tissue in the longissimus dorsi muscle relative to the hypothetical plane through the vertebrae and centerline of the specimen. For example, a connective tissue deposition angle of 0° would indicate connective tissue that is parallel to the plane through the centerline of the specimen and a connective tissue deposition angle of 90° would indicate connective tissue that is perpendicular to the plane. In actual specimen it has been determined that the angle of deposition ranges from approximately 15° to approximately 70° with tenderness decreasing with an increase in the angle of connective tissue deposition. In the present invention a specimen with connective tissue deposition angle of less than approximately 27° would yield the most tender meat and could be characterized as, for example, "tender". A specimen with a connective tissue deposition angle of approximately 27° to approximately 40° would yield the less tender meat and could be characterized as, for example, "acceptable". A specimen with a connective tissue deposition angle of greater than approximately 40° would yield the least tender meat and could be characterized as, for example, "tough". Other methods of categorization could be utilized as would be apparent to one of ordinary skill in the art including reporting the deposition angle of connective tissue as the tenderness indicator.

The connective tissue thickness, or density, has also been determined to be a factor in tenderness of the meat from a harvested animal. In practice, the connective tissue has been determined to range from approximately 1/32" thick to approximately 5/16" thick with the tenderness of the meat decreasing with increasing connective tissue thickness. Therefore, a specimen with a connective tissue density of less than approximately 1/8" would yield the most tender meat, a specimen with connective tissue density of approximately 1/8" to approximately 7/32" would be less tender and a specimen with a connective tissue density of more than 7/32" would be least tender.

It is most preferred that the measurement for tenderness be determined at a location of approximately 3/4 of the length (cranial to caudal) on the longissimus dorsi muscle at the $12^{th}$ rib to $1^{st}$ lumbar location.

After tenderness is determined the IMF, STRESS and TEND are reported at block 42.

STRESS is determined based on the consistency of the pixel density through the upper portion of the longissimus dorsi muscle. While not limited to any theory it is postulated that the pixel density, observed as a black area in the ultrasound image, increases with inferior diet. It is observed, through experimentation, that the larger the black area, representing unresolved image, the tougher the meat after harvest. Therefore, specimen with no black image area in the upper region of the longissimus dorsi muscle would be predicted to be the most tender after harvest. In practice, a specimen with a black area in the ultrasound corresponding to approximately the upper 10% of the longissimus dorsi muscle is considered to be low stress, or assigned a stress area level 1. A specimen with a black area in the ultrasound corresponding to approximately the upper 20% of the longissimus dorsi muscle is considered to be medium stress, or assigned a stress area level 2. A specimen with a black area in the ultrasound corresponding approximately to the upper 30%, or higher, of the longissimus dorsi muscle is considered to be high stress, or assigned a stress area level 3.

Echogenicity of the connective tissue can be enhanced through the use of commercially available neuro-networking and image enhancement subroutines without departing from the scope of the present invention.

Information derived from the REA, RES, FT, IMF, STRESS and TEND determinations are used to calculate predicted yield grade to be used in feedlot applications. A lower yield grade would indicate a specimen with a higher percentage of high quality meat per pound of specimen. A higher yield grade would indicate a lower percentage of high quality meat per pound of specimen. While not limited herein, the yield grade is determined based on the quality parameters REA, RES, FT, IMF, STRESS and TEND. A skilled artisan can provide a yield grade by combining these parameters with, or without, weighting factors based on the market conditions at the time of use or standards which could be established for consistency. At the time of the ultrasonic measurement a body weight for each animal will be entered. The calculated body fat and REA along with constants for estimated dressing percentage and kidney, pelvic and heart fat (KPH) are also used to derive predicted yield grade. Real time calculations and display of potential yield grade and quality grade can allow for chute side selection decisions.

The transmittal and receipt of ultrasound signal is preferably done with as high of a fidelity as possible to avoid spurious results and anomalies. More particularly the modulation transfer function of signal capture is preferably as close to unity as possible given the realistic conditions under which the measurement must be taken and the rapidity of measurements required in a standard operation. Towards this goal a preferred conforming guide is illustrated in FIG. 3.

In FIG. 3, the conforming guide generally represented at 100, is shown in partial cut-away view. The conforming guide comprises a collar, 101, which is rectangular and adapted to tightly receive the transducer in the central cavity, 102. The collar, 101, comprises an arch, 103, on each side which approximately conforms to the shape of the back of a specimen. A pliable seal, 104, receives the collar. As the conforming guide is brought into contact with the specimen the pliable seal, 104, conforms to the contour of the back of the specimen thereby forming a seal there between. An optional lip, 105, provides a convenient grip on the contour guide. The collar, 101, is preferably constructed of nylon due to the low cost, ready availability and ease of machining. The pliable seal, 104 is preferably constructed of Superflab Bolus available from Mick Radionuclear Instruments. Other pliable materials can be employed. It is most preferable that the pliable seal be easily conformed to the contour of the specimen yet resilient enough that the operator does not have to wait for a subsequent measurement while the pliable seal relaxes to an expanded state. The conforming guide can be utilized with, or without, a conductive fluid. The conforming guide is preferably used during a cross-sectional measurement but is preferably not used with a longitudinal measurement.

The conforming guide is shown in partial cutaway side view in FIG. 4. The dimensions of the conforming guide are chosen based on the size of the specimen and the size of the transducer. In a particularly preferred embodiment the collar is approximately 1.625 inches wide by approximately 9.5 inches long and approximately 1.75 inches high at the ends. The walls of the collar are preferably approximately 0.25 inches thick. The cavity is preferably approximately 9 inches long and 1.125 inches wide. The pliable seal is preferably 1.25 inches high and approximately 0.25 inches thick for the preferred material.

For the purposes of the present invention cattle are considered weaned at the point when the mother no longer supplies food and the animal is on feed exclusively. This is typically 195–215 days after birth and more preferably 200 to 210 days after birth. Most preferably, the cattle are weaned at 205 days after birth. The age at which a specimen is harvested is preferably 12 to 19 months. Between the weaning and harvesting the cattle are placed on a feeding program to enhance the yield of meat.

The present invention is specifically intended to be used with a computer wherein layer, and their thicknesses, are determined by computer algorithms. While not preferable, the present invention can be realized by human techniques such as by measuring a layer thickness from a monitor or from a hard copy printout of the image.

Experimental Results

A total of 97 weaned steers, randomly selected from a common herd, were maintained in a Calan Gate Individual Feeding System so that individual feed consumption could be recorded. All steers were ultrasonically scanned at weaning and at 30-day intervals up to the time of harvest. Data were collected for FT, REA, RES and IMF. Time of harvest was determined by FT as measured at the $12^{th}$ rib location, with the end point at 10 mm. At harvest, following a 48 hour chill, all carcasses were evaluated for quality grade and yield grade and actual carcass measurements were obtained for BF, REA, RES and IMF.

Data were analyzed to determine the ability of the system to accurately calculate ultrasound carcass measurements. Correlation coefficients were used to determine the degree of relationship between calculated estimates, Critical Vision software estimates and actual carcass data measurements were used as comparisons. Critical Vison software is available from Critical Vision Incorporated, Atlanta Ga. Pearson correlation coefficients from the sample comparing the REA determined by the inventive system with that calculated by Critical Vision was positive and significant ($r^2=0.90$, $p<0.05$). The correlation between the calculation of REA with the inventive system, measured five days prior to harvest, and actual carcass REA, measured after a 48 hour chill, was also highly significant and positive ($r^2=0.84$, $P<0.01$). The correlation between the estimate of REA by Critical Vision software and actual carcass REA was less reliable than the inventive system ($r^2=0.74$, $p<0.01$). These results indicate that the inventive system, utilizing recognition of image landmarks, is superior to currently available software.

Ribeye score (RES) was determined utilizing ultrasound at weaning and again at the end of the feeding phase. For an accurate estimate of REA, the RES must be consistent as the animal grows and develops. The degree of correlation between RES at weaning and RES at the end of the feeding phase was significant and positive ($r^2=0.62$, $p<0.05$).

To determine the predictability of carcass quality grade, calves were scanned at weaning and a predicted quality grade was assigned at that point based on estimates of IMF by the inventive system. Just prior to harvest, ultrasound IMF estimates were repeated. Correlation coefficients between the quality grade predicted at weaning and harvest time ultrasound IMF were significant and positive ($r^2=0.62$, $p<0.05$).

A separate comparison of tenderness predictability was undertaken on 97 steers. A tenderness score was assigned utilizing a longitudinal ultrasound image of the longissimus at the $12^{th}$ rib location a tenderness score was assigned in accordance with the inventive system. At harvest, a core sample was obtained from the 12$^{th}$ rib location from each steer. Each sample was cooked to the same degree of doneness and shear force estimates of tenderness were obtained by the Warner-Bratzler shear force measurement. The correlation coefficient was significant and positive ($r^2$= 0.72, p<0.05).

The invention has been describe with emphasis directed to the preferred embodiments. It would be apparent from the description herein that various embodiments could be developed without departing from the scope of the invention. Alternate methods of construction, operation and use could also be employed without departing from the scope of the invention which is set forth in the claims which follow.

What is claimed is:

1. A process for predicting meat tenderness in an animal comprising the steps of:

obtaining a longitudinal ultrasound measurement of a longissimus dorsi muscle of said animal;

determining an angle of connective tissue in said longissimus dorsi muscle relative to a centerline of said animal; and assigning a tenderness grade based on said angle of connective tissue wherein said tenderness grade comprises:

a first grade wherein said angle is less than approximately 27°;

a second grade wherein said angle is at least approximately 27° to approximately 40°; and a third grade wherein said angle is greater than approximately 40°.

2. A process for predicting meat tenderness in an animal comprising the steps of:

obtaining a longitudinal ultrasound measurement of a longissimus dorsi muscle of said animal;

determining an angle of connective tissue in said longissimus dorsi muscle relative to a centerline of said animal; and assigning a tenderness grade based on said angle of connective tissue wherein said angle is determined at a location of approximately ¾ the length of a longissimus doris muscle between the 12$^{th}$ rib and 1$^{st}$ lumbar.

* * * * *